(12) United States Patent
Robison (10) Patent No.: US 8,470,163 B2
(45) Date of Patent: Jun. 25, 2013

(54) EXHAUST GAS SENSOR AND METHOD OF MANUFACTURE

(75) Inventor: John Robison, Piedmont, SC (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/407,884

(22) Filed: Feb. 29, 2012

(65) Prior Publication Data

US 2012/0153535 A1 Jun. 21, 2012

Related U.S. Application Data (62) Division of application No. 11/613,530, filed on Dec. 20, 2006, now Pat. No. 8,147,667.

(51) Int. Cl.
*G01N 27/407* (2006.01)
(52) U.S. Cl.
USPC ........ 205/783.5; 204/410; 204/421; 249/117; 264/279; 264/279.1
(58) Field of Classification Search
USPC .................. 204/410, 411, 421–429; 205/781, 205/783.5–785, 787; 73/23.31, 23.32; 249/118–142; 264/279, 279.1
See application file for complete search history.

(56) References Cited

U.S. PATENT DOCUMENTS

| | | |
|---|---|---|
| 4,283,261 A | 8/1981 | Maurer et al. |
| 4,478,067 A | 10/1984 | Ohta et al. |
| 4,535,316 A | 8/1985 | Wertheimer et al. |
| 4,995,256 A | 2/1991 | Norlien et al. |
| 5,389,340 A | 2/1995 | Satake |
| 6,068,746 A | 5/2000 | Kojima et al. |
| 6,164,120 A | 12/2000 | Friese et al. |
| 6,319,376 B1 | 11/2001 | Graser et al. |
| 6,358,383 B2 | 3/2002 | Nelson et al. |
| 6,453,723 B1 | 9/2002 | Ichikawa et al. |
| 6,637,256 B2 | 10/2003 | Shirai |
| 2001/0035045 A1 | 11/2001 | Hibino et al. |
| 2001/0045120 A1 | 11/2001 | Friese et al. |
| 2004/0040370 A1 | 3/2004 | Kojima |
| 2004/0040843 A1 | 3/2004 | Weyl et al. |
| 2005/0224347 A1 | 10/2005 | Hahn et al. |

FOREIGN PATENT DOCUMENTS

| | | |
|---|---|---|
| DE | 102005020792 | 11/2006 |
| EP | 0520528 | 12/1992 |
| WO | 9838505 | 9/1998 |
| WO | 0134951 | 5/2001 |

OTHER PUBLICATIONS

Micaver HT product brochure, Saint-Gobain Quartz, Jan. 2004, 2 pages.

*Primary Examiner* — Alex Noguerola
*Assistant Examiner* — Gurpreet Kaur
(74) *Attorney, Agent, or Firm* — Michael Best & Friedrich LLP (57) ABSTRACT

A method of manufacturing an exhaust gas sensor that includes positioning at least a portion of a subassembly of the exhaust gas sensor in a mold fixture, overmolding at least a portion of the subassembly with a ceramic material, and removing the overmolded subassembly from the mold fixture.

13 Claims, 6 Drawing Sheets

EXHAUST GAS SENSOR AND METHOD OF MANUFACTURE

RELATED APPLICATIONS

This application is a divisional of U.S. patent application Ser. No. 11/613,530 filed Dec. 20, 2006, the entire content of which is hereby incorporated herein by reference.

BACKGROUND

The present invention relates to exhaust gas sensors.

Exhaust gas sensors help assure that an optimum air to fuel ratio is maintained in combustion engines. Typically, exhaust gas sensors are located in automobiles to compare the oxygen content of the exhaust with the oxygen content of surrounding air. Feedback from the sensor controls the amount of fuel injected into the engine. Planar type sensors and thimble type sensors are two common types of exhaust gas sensors. Planar type sensors include a flat ceramic sensor element. Thimble type sensors include a thimble-shaped sensor element.

SUMMARY

In one embodiment, the invention provides a method of manufacturing an exhaust gas sensor. The method includes positioning at least a portion of a subassembly of the exhaust gas sensor in a mold fixture, overmolding at least a portion of the subassembly with a ceramic material, and removing the overmolded subassembly from the mold fixture.

In another embodiment, the invention provides an exhaust gas sensor assembly that includes a housing, a sensor element partially received in the housing, and a ceramic material molded to the housing to encapsulate a portion of the sensor element.

In yet another embodiment, the invention provides an exhaust gas sensor assembly that includes a housing, a sensor element, and a sleeve coupled with the housing and the sensor element. The sleeve contains a ceramic material molded therein and defines a bore through which a conducting element extends.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

DETAILED DESCRIPTION

Figure 1:
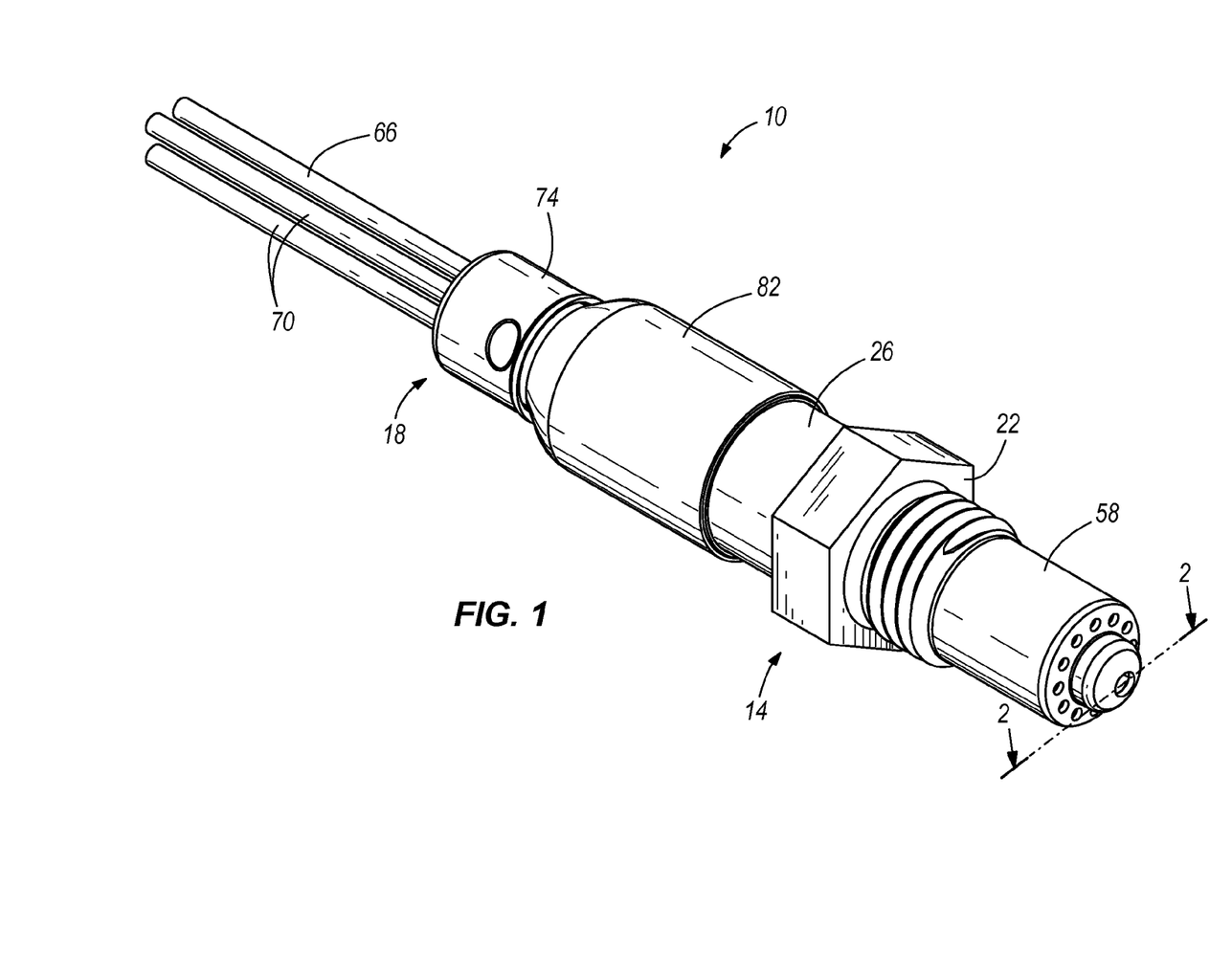
FIG. 1 is a perspective view of an exhaust gas sensor embodying the present invention.

FIG. 1 illustrates an exhaust gas sensor 10 of the present invention. The sensor 10 includes a sensor subassembly 14 and an exit lead or wire harness subassembly 18. The illustrated sensor subassembly 14, or short sensor assembly, includes a generally cylindrical metallic housing 22 configured to be threadably engaged with a threaded aperture of an exhaust pipe (not shown) or other component of an internal combustion engine used for automotive applications or non-automotive applications, such as motorcycles, snowmobiles, ATV's, lawnmowers, and the like.

Figure 2:
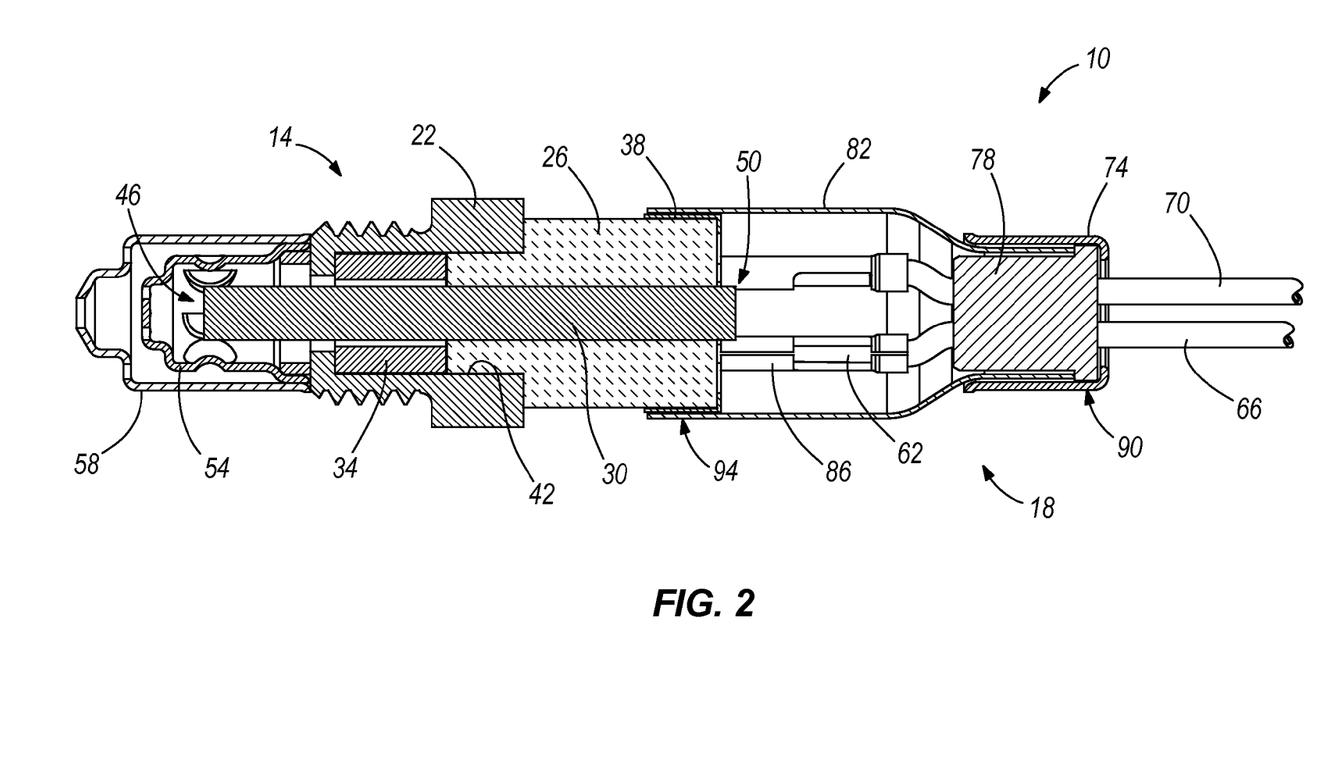
FIG. 2 is a cross-sectional view of the exhaust gas sensor shown in FIG. 1 taken along line 2-2 of FIG. 1.

Referring to FIG. 2, the illustrated sensor subassembly 14 also includes a ceramic material 26, a sensor element 30, a spacer 34, and a weld ring 38. The ceramic material 26 is molded to the housing 22 to encapsulate a middle portion of the sensor element 30 and to partially fill a bore 42 in the housing 22. During molding, the ceramic material 26 bonds to the housing 22 and the middle portion of the sensor element 30. In the illustrated construction, the ceramic material 26 is a MICAVER® HT mica material available from Saint-Gobain Quartz S.A.S. of France. The ceramic material 26 abuts the spacer 34, which in the illustrated embodiment is a sintered steatite bushing positioned in the housing 22 to act as a thermal barrier between the hot exhaust gases (e.g., greater than 700 degrees Celsius) and the ceramic material 26. In the illustrated embodiment, the spacer 34 prevents the ceramic material 26 from entirely filling the bore 42 of the housing 22. In some low temperature applications, the spacer 34 can be eliminated, with the ceramic material 26 filling more of the bore 42. The ceramic material 26 also bonds to the weld ring 38 to support the weld ring 38 apart from the housing 22. The weld ring 38 provides a coupling area for the wire harness subassembly 18 as will be further described below.

In the illustrated construction, the sensor element 30 is a planar type sensor. Reference is made to U.S. Pat. No. 6,164,120, filed on Dec. 16, 1997, the entire contents of which are incorporated herein by reference, for discussion of additional features and operations of the planar type sensor not described herein. The sensor element 30 has a first end 46 extending out from one end of the ceramic material 26 and a second end 50 extending out from the opposite end of the ceramic material 26. In the illustrated embodiment, the first end or exhaust side 46 of the sensor element 30 is surrounded by an inner protection tube 54 and an outer protection tube 58. The exhaust side 46 of the sensor element 30 is exposed to exhaust gas generated by the internal combustion engine.

The second end or reference side 50 of the sensor element 30 is surrounded by the wire harness subassembly 18 and is exposed to reference air from the environment. However, in other constructions (not shown), the ceramic material 26 may also encapsulate the reference side 50 of the sensor element 30 and an air channel is molded or formed (e.g., by drilling) in the ceramic material 26 to allow communication of the sensor element 30 with the reference air.

In the illustrated embodiment, four terminal pins or weld pins 62 electrically couple to the sensor element 30 by, for example, resistance welding or brazing. The ceramic material 26 partially encapsulates the terminal pins 62 such that one end of each terminal pin 62 extends from the ceramic material 26. The terminal pins 62 facilitate electrical contact between the wire harness subassembly 18 and the sensor element 30. In other embodiments, fewer or more terminal pins may be used.

The wire harness subassembly 18 includes signal wires 66, heater wires 70, a cap 74, a seal grommet 78, and a sleeve 82. Weld terminals 86 are positioned on each wire 66, 70 and electrically couple with the corresponding terminal pins 62 of the sensor subassembly 14 by resistance welding or other suitable alternatives. The illustrated wire harness subassembly 18 includes four wires 66, 70 and weld terminals 86. However, it should be readily apparent to one skilled in the art that the wire harness subassembly 18 could be modified to include fewer or more wires 66, 70 and weld terminals 86 to match the number of terminal pins 62 of the sensor subassembly 14.

The seal grommet 78 is positioned partially within a first end 90 of the sleeve 82 to support the wires 66, 70. The cap 74 secures the seal grommet 78 in place and couples to the first end 90 of the sleeve 82 by crimping or other suitable securing operations (e.g., brazing, welding, adhesives, etc.). The wire harness subassembly 18 couples to the weld ring 38 of the sensor subassembly 14 at a second end 94 of the sleeve 82 by press fitting and laser welding. Of course, other suitable securing operations may also be used.

Figure 3:
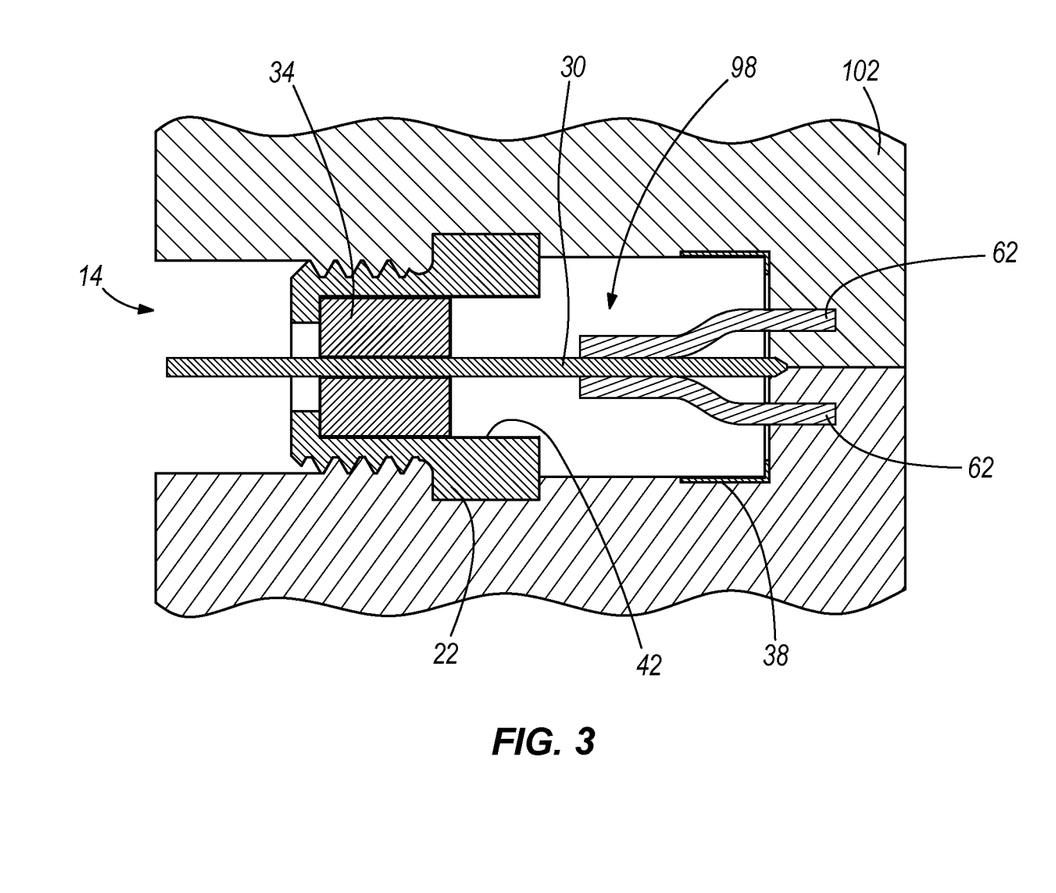
FIG. 3 is a cross-sectional view of a subassembly of the exhaust gas sensor shown in FIG. 1 positioned within a mold fixture.

The exhaust gas sensor 10 is manufactured by positioning the sensor subassembly 14, minus the ceramic material 26, within a mold cavity 98 of a mold fixture 102, as shown in FIG. 3. Liquefied or flowable ceramic material is injected (e.g., forced under pressure) into the mold cavity 98, overmolding a portion of the housing 22 and partially filling the bore 42 of the housing 22. The injected ceramic material also overmolds and partially surrounds the middle portion of the sensor element 30 and portions of the terminal pins 62. As the injected ceramic material cools, the ceramic material 26 hardens, thereby bonding to the housing 22. Also during hardening, the ceramic material 26 bonds to and encapsulates the middle portion of the sensor element 30 and portions of the terminal pins 62, forming a hermetic seal about the middle portion of the sensor element 30 and the terminal pins 62. The weld ring 38 is positioned in the mold cavity 98 apart from the housing 22 such that as the injected ceramic material cools, the ceramic material 26 also bonds to the weld ring 38. Once the ceramic material 26 hardens, the overmolded sensor subassembly 14 is removed from the mold cavity 98. The bonding of the ceramic material 26 to the housing 22, the sensor element 30, the terminal pins 62, and the weld ring 38 integrates the sensor subassembly 14 into a single, inseparable piece.

Figure 4:
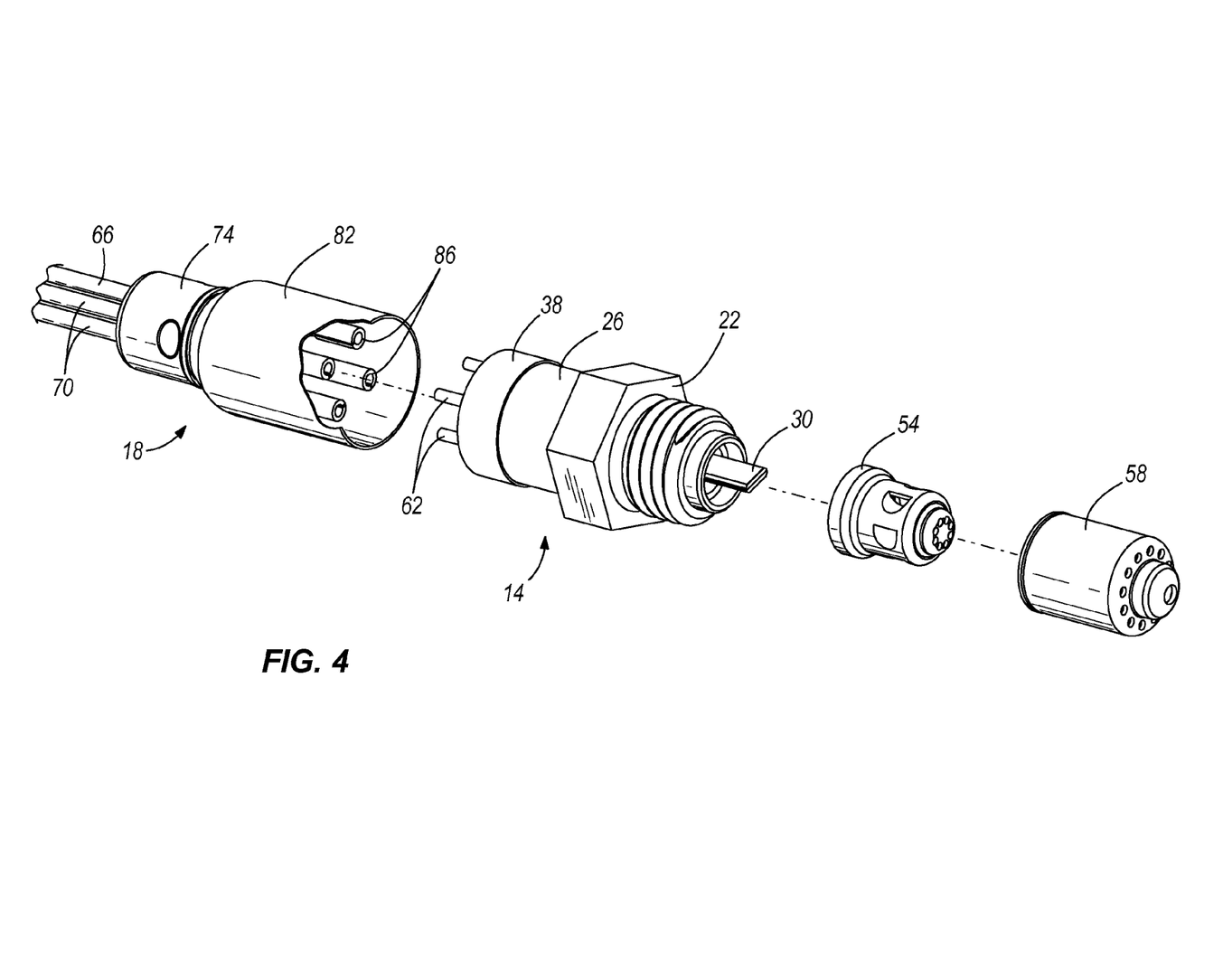
FIG. 4 is a partially exploded perspective view of the components of the exhaust gas sensor shown in FIG. 1.

FIG. 4 illustrates the overmolded sensor subassembly 14 separated from the wire harness subassembly 18. After the overmolded sensor subassembly 14 is removed from the mold fixture 102, the inner protection tube 54 and the outer protection tube 58 are coupled to the housing 22 adjacent to the exhaust side 46 of the sensor element 30 by crimping, welding, or other suitable methods. The wire harness subassembly 18 components are assembled apart from the sensor subassembly 14, and are then coupled to the sensor subassembly 14 by first resistance welding the weld terminals 86 to the terminal pins 62 and then press fitting and laser welding the sleeve 82 to the weld ring 38.

The illustrated exhaust gas sensor 10 reduces the total number of components required for construction. For example, prior art exhaust gas sensors use steatite packing and boron nitride packing positioned about the middle portion of the sensor element to seal the reference side from the exhaust side. These packings are susceptible to characteristic shift downward (CSD) problems due to fuel vapor contamination. In the illustrated exhaust gas sensor 10, both the steatite packing and boron nitride packing are replaced by the ceramic material 26, which acts as a hermetic seal and is less susceptible to CSD.

In addition, the illustrated exhaust gas sensor 10 reduces the complexity and size of the manufacturing process required. Not only are the number of components required reduced, but the sensor element length may also be reduced compared to currently used exhaust gas sensors.

The illustrated exhaust gas sensor 10 also provides an insulating barrier between the metal components (e.g., the housing 22 and the sleeve 82) to prevent excess conduction of heat to sensitive components, such as the seal grommet 78 and the wires 66, 70. The ceramic material 26 is a highly insulative barrier that prevents the transfer of heat from the exhaust side 46 of the sensor element 30 to the reference side 50. The ceramic material 26 improves thermal operating characteristics of the exhaust gas sensor 10 by breaking the metal to metal contact and having a low thermal conductivity (about 0.8 W/m·K) compared to steatite bushings (about 1.6 W/m·K) or stainless steel (about 14 W/m·K).

Furthermore, the ceramic material 26 retains and isolates the terminal pins 62 to withstand high pull forces and vibrations. In other words, pull forces and vibrations that might otherwise cause separation between the sensor element 30 and the terminal pins 62 do not cause such separation in the illustrated exhaust gas sensor 10 due to the overmolded ceramic material 26.

Figures 5, 6:
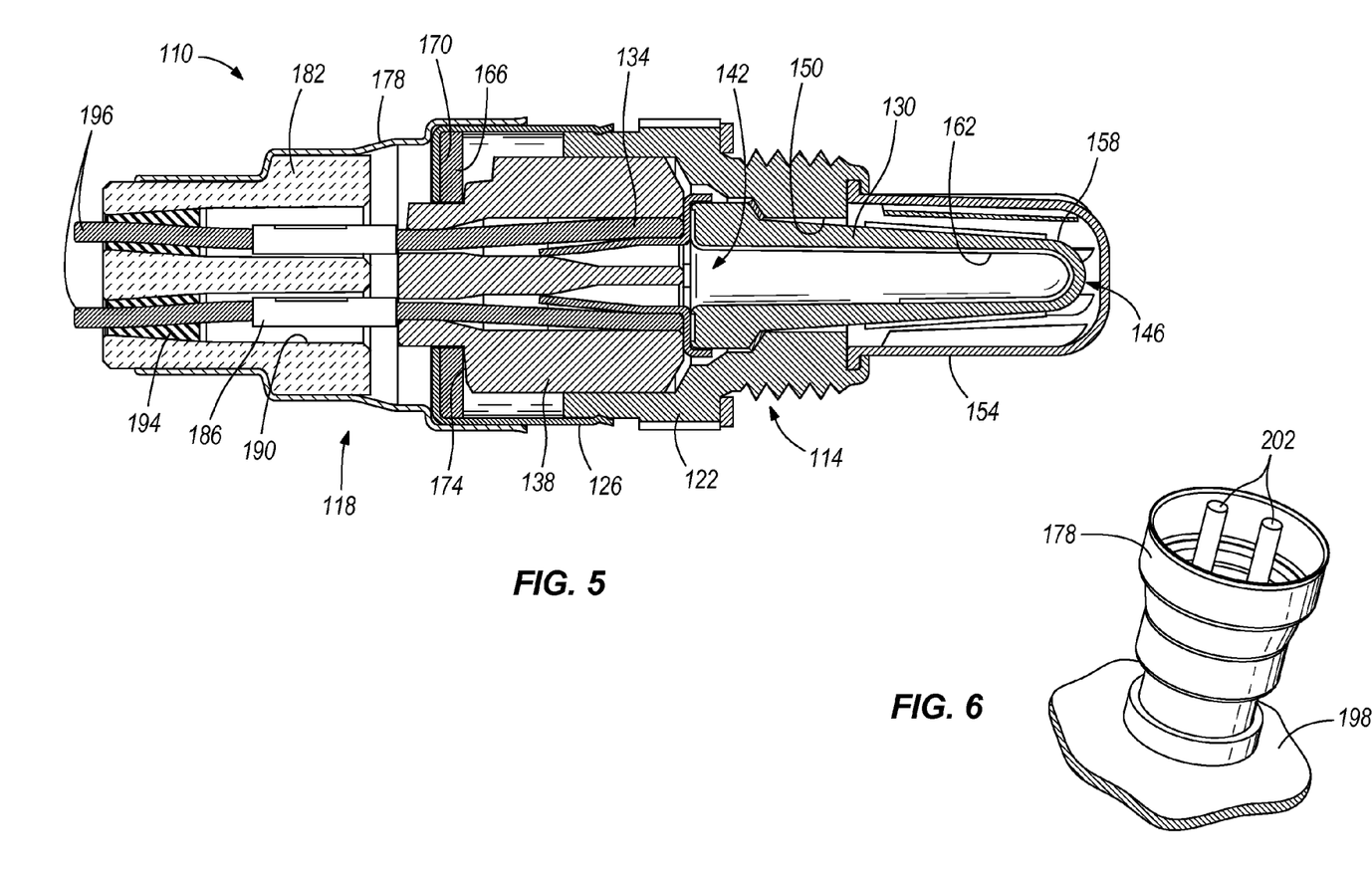
FIG. 5 is a cross-sectional view of another construction of an exhaust gas sensor embodying the present invention.
FIG. 6 is a perspective view of a portion of the exhaust gas sensor shown in FIG. 5 positioned on a mold fixture.

FIG. 5 illustrates another construction of an exhaust gas sensor 110 of the present invention. The exhaust gas sensor 110 includes a sensor subassembly 114 and a wire harness subassembly 118. The sensor subassembly 114 includes a housing 122 functioning in the same manner as the housing 22 of the previous embodiment, a weld ring or sleeve 126 directly coupled to the housing 122, a sensor element 130, conducting elements 134, and a bushing 138.

In the illustrated construction, the sensor element 130 is a cup-shaped ceramic member, or thimble type sensor. Reference is made to pending U.S. Patent Application Publication No. 2005/0224347A1, filed on Apr. 12, 2004, the entire contents of which are incorporated herein by reference, for discussion of additional features and operations of the thimble type sensor not described herein. The sensor element 130 includes an open end 142 and a closed end 146. The sensor element 130 is positioned partially within a bore 150 of the housing 122 such that the closed end 146 extends out of the housing 122. A protection tube 154 couples to the housing 122 (e.g., by crimping) and surrounds the closed end 146 to protect the sensor element 130 and temporarily trap the exhaust gas adjacent to an outer surface 158 of the sensor element 130. The open end 142 of the sensor element 130 allows the reference air to communicate with an inner surface 162 of the sensor element 130. The conducting elements 134 electrically couple to the sensor element 130 adjacent to the open end 142. In the illustrated construction, two conducting elements 134 are shown. However, it should be readily apparent to one skilled in the art that fewer or more conducting elements 134 may be coupled to the sensor element 130.

Most of the bushing 138 is positioned inside the weld ring 126 and the bore 150 of the housing 122. The bushing 138 surrounds the conducting elements 134 to insulate and support the conducting elements 134. A disc spring 166 positioned adjacent an inner surface 170 of the weld ring 126 engages a shoulder 174 of the bushing 138 to bias the bushing 138 toward the housing 122.

The wire harness subassembly 118 includes a sleeve or harness cap 178, a ceramic material 182, and weld terminals 186. The sleeve 178 is coupled to the weld ring 126 in a manner similar to the sleeve 82 and weld ring 38 of the previous embodiment. The ceramic material 182, which is a MICAVER® HT mica material available from Saint-Gobain Quartz S.A.S. of France, partially fills and molds or bonds to an inner surface of the sleeve 178. The lead wires 186 partially extend through bores 190 in the ceramic material 182 and electrically couple with the conducting elements 134 by resistance welding. Wire seals 194 (e.g., Viton® seals available from DuPont Performance Elastomers L.L.C. of Wilmington, Del.) surround lead wires 196 coupled to the weld terminals 186 and seal the end of the wire harness subassembly 118.

In one embodiment, the exhaust gas sensor 110 is manufactured by positioning the sleeve 178 on a mold fixture 198, as shown in FIG. 6. The mold fixture 198 may or may not define a mold cavity. The mold fixture 198 includes two plugs 202 positioned to create the bores 190 in the ceramic material 182. However, it should be readily apparent to one skilled in the art that fewer or more plugs 202 may be included to correspond with the number of weld terminals 186, and therefore conducting elements 134, of the sensor 110. Liquefied or flowable ceramic material (not shown) is injected (e.g., forced under pressure) into the sleeve 178 to partially fill the sleeve 178. As the injected ceramic material cools, the ceramic material 182 hardens and bonds to the sleeve 178. Once the ceramic material 182 has hardened, the sleeve 178 is removed from the mold fixture 198. In another construction, the bores 190 may be formed (e.g., by drilling) after the ceramic material 182 hardens.

Figure 7:
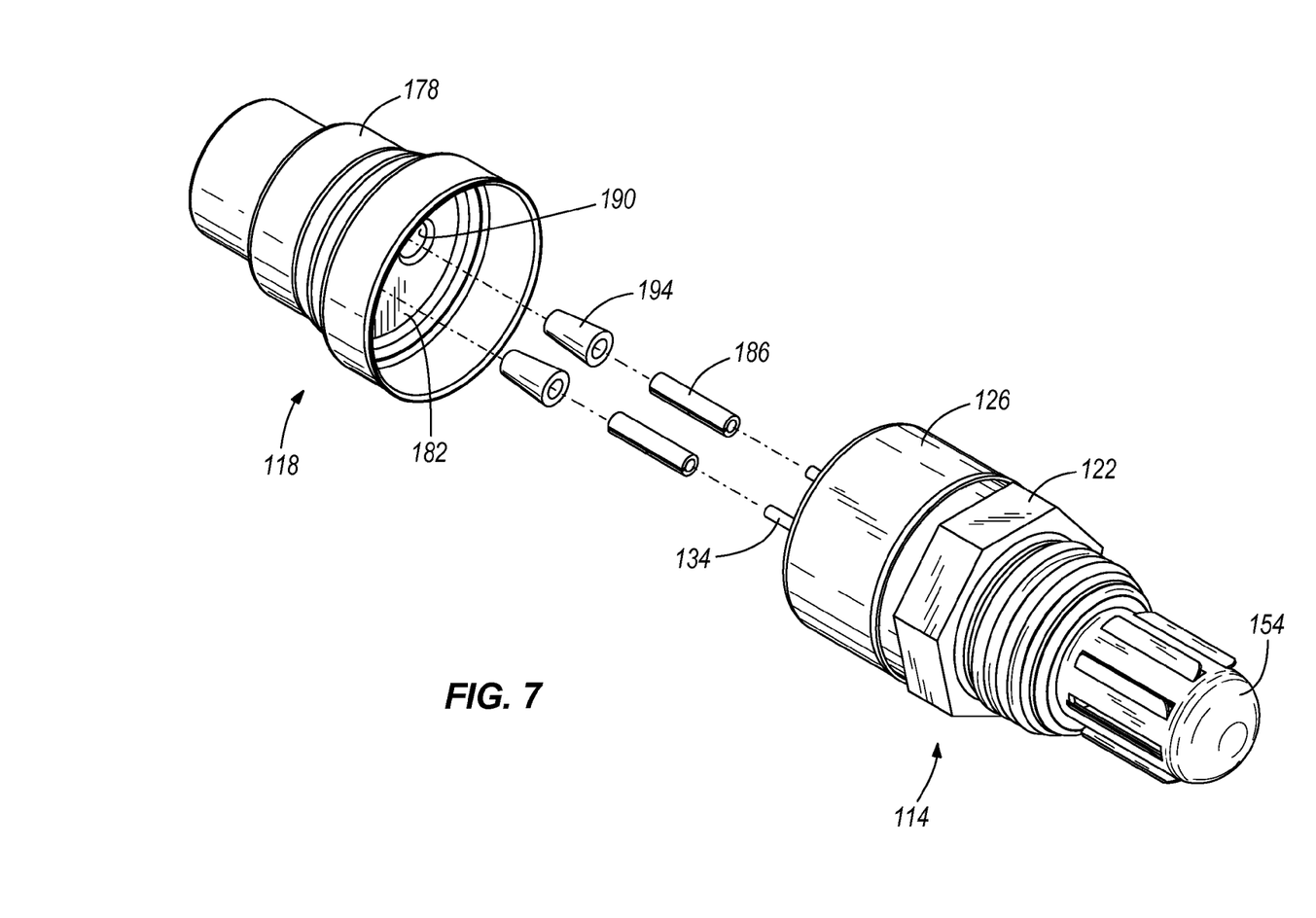
FIG. 7 is a partially exploded perspective view of the components of the exhaust gas sensor shown in FIG. 5.

FIG. 7 illustrates the sleeve 178 and the overmolded ceramic material 182 separated from the sensor subassembly 114. After the sleeve 178 is removed from the mold fixture 198, the seals 194 are inserted into the bores 190 of the ceramic material 182. The weld terminals 186 are coupled to the conducting elements 134 and the lead wires 196 by resistance welding and then slid into the bores 190. The assembled wire harness subassembly 118 is then attached to the sensor subassembly 114 by press fitting and laser welding the sleeve 178 to the weld ring 126.

Prior art wire harness subassemblies require a structural grommet (similar to the seal grommet 78 shown in FIG. 2) made of polytetraluoroethylene (PTFE) positioned in the sleeve to insulate and support the lead wires 196. The structural grommet is a separable component of the wire harness subassembly and, therefore, requires a cap or other fixating structure to hold the grommet in the sleeve. In addition, an O-ring is positioned in the sleeve adjacent to the structural grommet to ensure proper sealing between the structural grommet and the sleeve.

The ceramic material 182 of the illustrated exhaust gas sensor 110 replaces the structural grommet, thereby allowing higher operating temperatures and effectively reducing the amount of heat transferred from the exhaust gas to the wire seals 194. In addition, the ceramic material 182 bonds to the sleeve 178 so a cap is not necessary to hold the ceramic material 182 inside the sleeve 178 and an O-ring is not necessary to seal between the ceramic material 182 and sleeve 178.

The ceramic material 182 also reduces the risk of damage to other PTFE and fluorocarbon rubber components of the wire harness subassembly 118 such as, for example, the wire seals 194.

Although the exhaust gas sensors 10, 110 and respective ceramic materials 26, 182 were discussed with reference to different sensor element types, it should be readily apparent to one skilled in the art that the wire harness subassembly 118 of the thimble type sensor 110 may be adapted and configured to replace the wire harness subassembly 18 of the planar type sensor 10. That is, for example, the ceramic material 182 illustrated in FIG. 5 may be molded into the cap 74 to replace the seal grommet 78 illustrated in FIG. 2. Additionally, the bushing 138 in the sensor subassembly 114 of the sensor 110 could be replaced by a molded-in ceramic material in the same manner as described for the ceramic material 26 of the sensor 10.

Various features and advantages of the invention are set forth in the following claims.

What is claimed is:

1. A method of manufacturing an exhaust gas sensor having a subassembly including a housing, a sensor element, and a weld ring, the method comprising:
   positioning at least a portion of the housing and at least a portion of the sensor element in a cavity of a mold fixture;
   positioning the weld ring in the mold cavity apart from the housing;
   injecting a ceramic material into the mold cavity to overmold at least a portion of the housing and at least a portion of the sensor element, and to mold the ceramic material to the weld ring; and
   removing the overmolded subassembly from the mold fixture.

2. The method of claim 1, wherein injecting the ceramic material at least partially encapsulates the sensor element.

3. The method of claim 2, wherein the subassembly includes a terminal pin electrically coupled to the sensor element, and the method further comprising coupling a wire to the terminal pin.

4. The method of claim 3, wherein injecting the ceramic material at least partially encapsulates the terminal pin.

5. The method of claim 1, wherein injecting the ceramic material results in bonding of the ceramic material to the housing.

6. The method of claim 5, wherein the housing includes a bore, and wherein injecting results in the ceramic material at least partially filling the bore.

7. The method of claim 1, further comprising coupling a wire harness sleeve to the weld ring.

8. The method of claim 7, wherein coupling the wire harness sleeve to the weld ring includes welding the wire harness sleeve to the weld ring.

9. The method of claim 7, wherein the ceramic material provides an insulating barrier between the housing and the wire harness sleeve.

10. The method of claim 9, wherein the ceramic material is a mica material.

11. The method of claim 1, wherein injecting the ceramic material results in bonding of the ceramic material to the sensor element.

12. The method of claim 1, wherein injecting the ceramic material results in forming a hermetic seal between the ceramic material and the sensor element.

13. The method of claim 1, wherein injecting the ceramic material results in bonding of the ceramic material to the weld ring.

* * * * *